United States Patent [19]

Nakamura et al.

[11] Patent Number: 5,116,114
[45] Date of Patent: May 26, 1992

[54] OPHTHALMOLOGIC APPARATUS

[75] Inventors: Yukitsugu Nakamura, Sagamihara; Yoshimasa Hamano, Yamato; Takashi Masuda, Kawasaki; Isao Matsumura, Yokosuka; Shigeo Maruyama, Machida; Kazunobu Kobayashi, Yokohama, all of Japan

[73] Assignee: Canon Kabushiki Kaisha, Tokyo, Japan

[21] Appl. No.: 767,360

[22] Filed: Sep. 30, 1991

Related U.S. Application Data

[63] Continuation of Ser. No. 609,097, Nov. 5, 1990, abandoned, which is a continuation of Ser. No. 248,042, Sep. 23, 1988, abandoned.

[30] Foreign Application Priority Data

Sep. 30, 1987 [JP] Japan .................... 62-250536
Jan. 12, 1988 [JP] Japan .................... 63-004030
Mar. 23, 1988 [JP] Japan .................... 63-070298

[51] Int. Cl.⁵ .................................. A61B 3/10
[52] U.S. Cl. .................................. 351/205; 351/211; 351/214; 606/4
[58] Field of Search ............... 351/205, 211, 214, 245, 351/208; 128/303.1, 76.5; 606/4

[56] References Cited

U.S. PATENT DOCUMENTS

3,070,997 1/1963 Papritz et al. ............... 351/214
3,453,998 7/1969 Giglio .
4,764,006 8/1988 Hamano et al. .

Primary Examiner—Rodney B. Bovernick
Attorney, Agent, or Firm—Fitzpatrick, Cella, Harper & Scinto

[57] ABSTRACT

An ophthalmologic apparatus can measure the eye axis length of an eye to be examined and other information of the eye to be examined (for example, the cornea refractive power). In the case of the measurement of the eye axis length, when moving a detecting terminal itself by driving means, the driving means is controlled so as to slow down the speed of movement of the detecting terminal when the detecting terminal comes near the cornea of the eye to be examined.

15 Claims, 7 Drawing Sheets

OPHTHALMOLOGIC APPARATUS

This application is a continuation of application Ser. No. 07/609,097 filed Nov. 5, 1990, now abandoned; which is a continuation of application Ser. No. 07/248,042, filed Sep. 23, 1988, now abandoned.

BACKGROUND OF THE INVENTION

1. Field of the Invention

This invention relates to an ophthalmologic apparatus having a plurality of measuring and examining functions requiring different working distances, such as measuring the cornea refractive power and measuring the eye axis length.

2. Related Background Art

Heretofore, a spectacle lens or a contact lens has been used to correct the refractive power of the eye after a surgical cataract operation, but in recent years, it has been practised to insert an in-the-eye lens into the position of the removed crystalline lens. To choose a proper in-the-eye lens for a patient having an eye without a crystalline lens, it is necessary to know the cornea refractive power and the eye axis length, i.e., the length from the cornea to the retina.

In the past, however, there has been the inconvenience that the measurement of the cornea refractive power is effected by a cornea shape measuring apparatus and the measurement of the eye axis length is effected by a discrete ultrasonic measuring apparatus, from which the refractive power of the in-the-eye lens must be calculated.

An apparatus having the both functions is proposed in U.S. application Ser. No. 906,271 now U.S. Pat. No. 4,764,006. In this case, it is desired that during the measurement of the shape of the cornea, the corneal reflection image not be eclipsed by the image of an eye axis length measuring probe which is present in the optical path.

It is also desirable to eliminate the necessity that the system for measuring the eye axis length be optically transparent.

Further, an apparatus in which a slidable bed need not be moved in a horizontal plane is desirable because an attempt to effect two measurements by moving the slidable bed in a horizontal plane in the direction of the optic axis results in the destruction of the alignment in a direction perpendicular to the optic axis.

U.S. application Ser. No. 162,250 now abandoned has been proposed as an apparatus which satisfies these requirements, but it is desired that consideration be given to the safety of the cornea of an eye to be examined when an eye axis length measuring probe (a detecting terminal) is brought close to the cornea of the eye to be examined by driving means.

SUMMARY OF THE INVENTION

It is an object of the present invention to provide an ophthalmologic apparatus which can accomplish the measurement of the cornea refractive power and the measurement of the eye axis length with a slidable bed remaining fixed in a horizontal plane.

It is also an object of the present invention to provide an ophthalmologic apparatus in which during the measurement of the shape of the cornea, an eye axis length measuring probe does not adversely affect the measurement of the shape of the cornea.

It is a further object of the present invention to provide an apparatus in which consideration is given to the safety of the cornea of an eye to be examined when a detecting terminal is brought close to the cornea of the eye to be examined by driving means.

BRIEF DESCRIPTION OF THE DRAWINGS

FIGS. 6 to 8 show the constructions of second to fourth embodiments, respectively.

DESCRIPTION OF THE PREFERRED EMBODIMENTS

Figure 1:
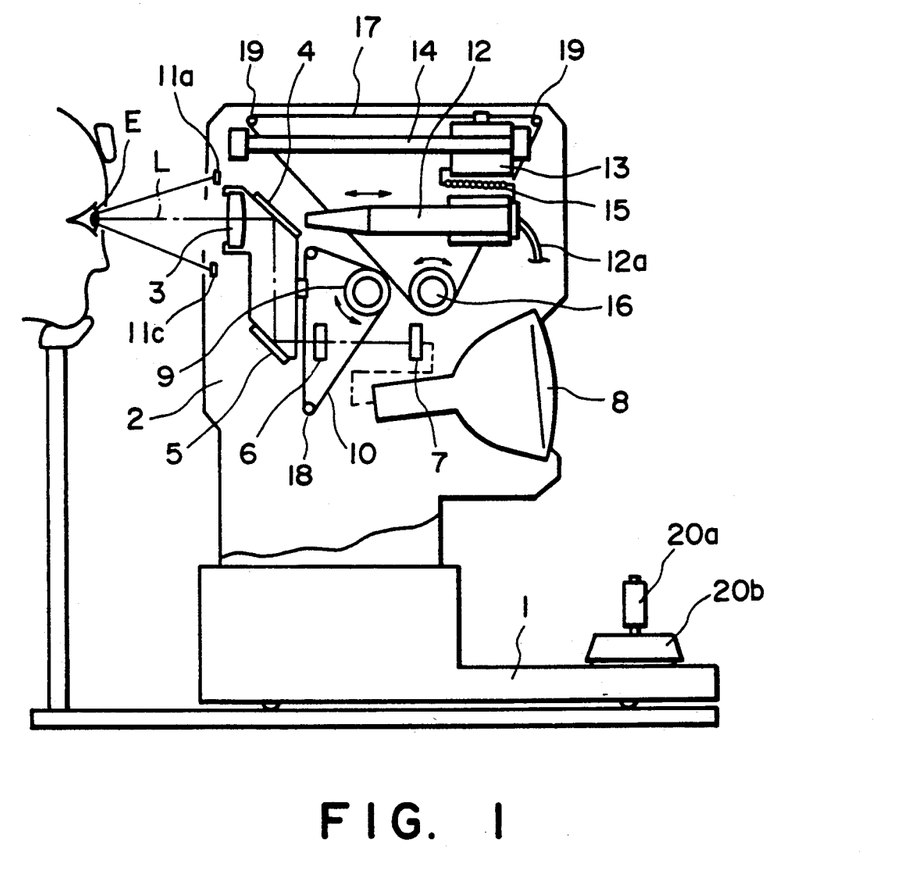
FIG. 1 shows the general construction of an embodiment of the present invention.
Figure 2:
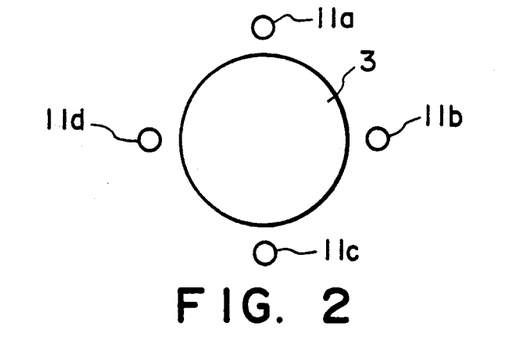
FIG. 2 is a front view showing an example of the arrangement of projection index light sources.

Referring to FIG. 1, a first measuring system for measuring the cornea refractive power of an eye E to be examined and a second measuring system for finding the eye axis length are provided in a body 2 provided on a slidable bed 1. In the first measuring system, an objective lens 3 is disposed in opposed relationship with the eye E to be examined, and rearwardly thereof, mirrors 4 and 5, an imaging lens 6 and a two-dimensional image pickup element 7 comprising a CCD or the like are disposed along the optical path, the output of the two-dimensional image pickup element 7 being connected to a television monitor 8. The objective lens 3 and mirrors 4 and 5 are of unitary structure and are vertically movable by a wire 10 driven by an electric motor 9. Also, around the objective lens 3, a plurality of projection index light sources 11a-11d each comprising a light-emitting diode are disposed at equal intervals about the optic axis L, as shown in FIG. 2. Further, in the second measuring system, an ultrasonic probe 12 (to which a cable 12a is connected) disposed rearwardly of the mirror 4 is held by a slidable guide member 14 through a probe holder 13, and this ultrasonic probe 12 is biased forwardly by a tension spring 15. The probe holder 13 is movable back and forth by a wire 17 moved by an electric motor 16. In FIG. 1, the reference numerals 8 and 19 designate guide rollers for guiding the wires 10 and 17, respectively, the reference character 20a denotes an operating rod, and the reference character 20b designates a vertical movement adjusting ring.

When the projection index light sources 11a-11d are projected onto the cornea of the eye E to be examined with a predetermined spatial distance provided therebetween the corneal reflection images of the projection index light sources 11a-11d are formed by the convex mirror action of the cornea, and it is well known that the correlation between the light spot positions of these corneal reflection images varies in conformity with the radius of curvature of the cornea and the magnitude of the degree of astigmatism and therfore, by detecting such variation, the cornea refractive power, the degree of astigmatism of the cornea and the axis angle can be found.

The first measuring system detects the corneal reflection images of the projection index light sources 11a–11d by causing such corneal reflection images to be formed on the two-dimensional image pickup element 7 by an optical system comprising the objective lens 3, the mirrors 4 and 5 and the imaging lens 6. This detection signal is processed in an electric circuit, not shown, and is further operation-processed to thereby find the cornea refractive power, the degree of astigmatism of the cornea and the axis angle. The two-dimensional image pickup element 7 can be utilized not only for the detection of a measurement signal, but also as a mechanism for observing the front eye part of the eye E to be examined, and is adapted so that it can be aligned by operating the slidable bed 1 while observing the front eye part by means of the television monitor 8.

As regards the second measuring system, an ultrasonic wave oscillator and a receiver are contained in the probe 12 and are connected to an electric circuit portion, not shown, through the cable 12a. An ultrasonic pulse is oscillated from the fore end of the ultrasonic probe 12 with the probe 12 being brought into contact with the cornea of the eye E to be examined, and the reflected echo from the retina of the eye E to be examined is received, whereby the eye axis length from the surface of the cornea to the retina can be detected and a measured value can be found, as is well known.

It is also well known that after the cornea refractive power and the eye axis length of the eye E to be examined are measured in this manner, the refractive power of an artificial crystalline lens can be calculated from a calculation formula empirically obtained.

Figure 3:
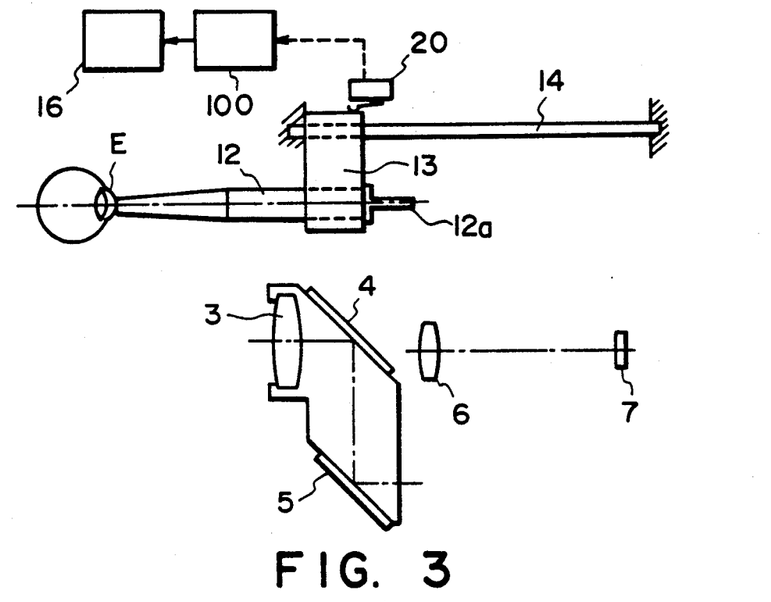
FIG. 3 shows the case of eye axis length measurement in a first embodiment.

In the present embodiment, during the measurement of the cornea refractive power, the ultrasonic probe 12 is retracted rearwardly of the mirror 4 so as not to hamper the cornea refractive power measuring optical path, but when the mode is changed over to the eye axis angle measuring mode by a change-over switch, not shown, the objective lens 3 and the mirrors 4 and 5 are lowered, and then the probe 12 is moved forward until it contacts the cornea of the eye E to be examined, thus assuming the state shown in FIG. 3. At this time, the lowering movement of the objective lens 3 and the mirrors 4 and 5 is accomplished by the electric motor 9 and the wire 10. Likewise, the movement of the probe 12 is accomplished by the electric motor 16 and the wire 17.

Here, the design is made such that the position of the fore end of the ultrasonic probe 12 during the measurement of the eye axis length is substantially brought into coincidence with the position of the cornea of the eye E to be examined during the measurement of the cornea refractive power, or is somewhat protruded in the direction of the optic axis. By doing so, during the measurement of the cornea refractive power, a proper alignment operation is performed while the television monitor 8 is observed, whereafter even if readjustment of the alignment is not done when the mode is changed over to the eye axis length measuring mode, the fore end of the probe 12 is moved forward to a position in which it contacts with the cornea, and the measurement of the eye axis length can be done immediately. If a long time is required for the change-over operation, there will be the possibility that the patient moves and the position of the cornea becomes improper, but in the present embodiment, the movement during the change-over operation is accomplished quickly by the electric motor 16 and therefore, the risk of the cornea moving is small.

Also, when only the eye axis length is to be measured, the slidable bed 1 including the ultrasonic probe 12 can be moved while the fore end of the ultrasonic probe 12 is being watched, but the measuring operation will be easier and more efficient if the mode is once changed over to the cornea refractive power measuring mode and the alignment by the slidable bed 1 is effected while the television monitor 8 is observed, whereafter the mode is changed over to the eye axis length measuring mode and the probe 12 itself is moved by the electric motor 16.

Now, the ultrasonic probe 12 is held by the probe holder 13 so as to be slidable back and forth, i.e., in the direction of the measuring optic axis L, with a low frictional force, and also is biased forwardly by a weak tension spring 15. Therefore, even if the probe 12 is brought too close to the eye E to be examined, the probe 12 is retracted against the weak force of the tension spring 15, whereby the end surface of the probe 12 is brought into contact with the cornea of the eye E to be examined with a predetermined weak pressure and thus, there is no danger of forcing the cornea to be dented or injured.

Figure 4:
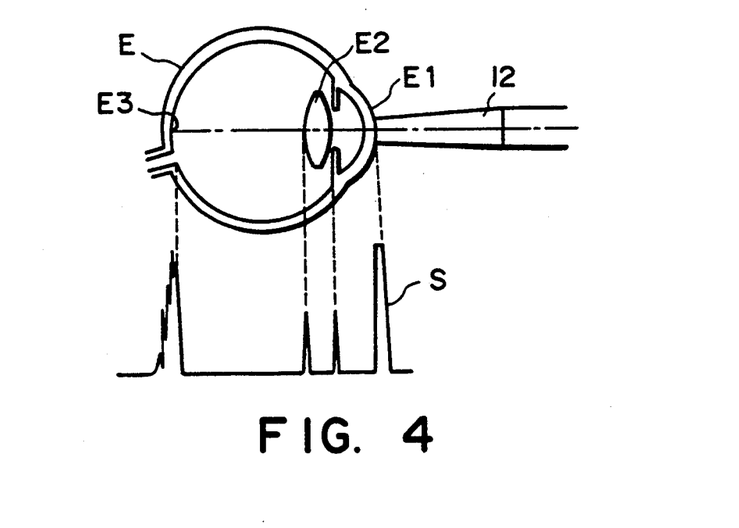
FIG. 4 is a cross-sectional view of an eye to be examined and an illustration of a signal wave form.

In the above-described embodiment, the ultrasonic probe 12 is moved forward when the mode is changed over to the eye axis length measuring mode, and when the fore end thereof comes into contact with the cornea of the eye E to be examined, the ultrasonic echo signals of the cornea surface, the fore and rear pouches of the crystalline lens and the retina are detected as shown in FIG. 4, and particularly the signal S of the cornea surface appears remarkably. When this ultrasonic signal S of the cornea surface is detected, the driving power source of the electric motor 16 may be cut off so as to stop the movement of the probe holder 13. Alternatively, a structure may be adopted in which the movement of the probe holder 13 is stopped at a position advanced by several millimeters from the position at which the ultrasonic signal of the cornea surface has been detected, whereby the probe 12 contacts with the cornea while having the after pressure by the tension spring 15.

Here, in the stroke wherein the ultrasonic probe is moved, the embodiment is made such that the probe 12 is moved at a high speed until it comes near the cornea of the eye E to be examined, and the probe 12 is moved at a low speed after it has come near the cornea. As a first embodiment, when as shown in FIG. 3, the probe holder 13 is moved toward the eye E to be examined, a driving voltage is given to the electric motor 16 by a motor control circuit 100 so that the probe holder is moved at a high speed until it contacts a microswitch 20 provided in the course of the movement stroke, and if the probe holder 13 is detected by the microswitch 20, the driving voltage to the electric motor 16 is reduced by the motor control circuit 100, whereby the number of revolutions of the electric motor 16 is reduced to thereby slow down the movement velocity of the probe holder 13. Thus, the change-over time can be shortened and the danger of the probe 12 striking against the cornea with a strong inertia force can be avoided.

After the measurement is completed, the motors 16 and 9 are controlled so as to revolve in the reverse direction and the restoring operation is performed in the above-described procedure to thereby bring the apparatus back to the state shown in FIG. 1.

Figure 5:
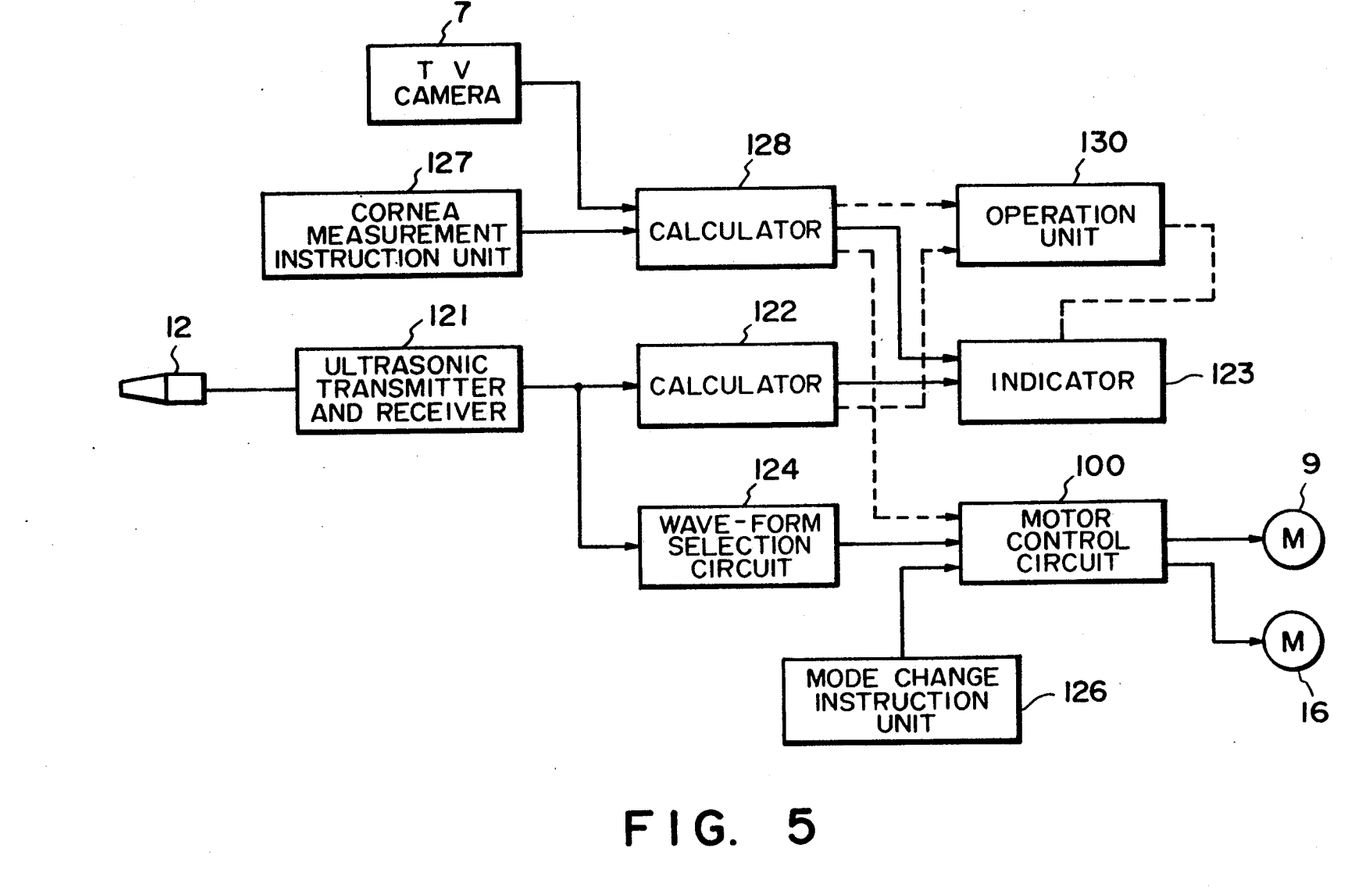
FIG. 5 is a block diagram of an electric circuit.

Here, the control and calculation procedures of the ophthalmologic apparatus of the present embodiment will be described with reference to the block diagram of FIG. 5.

For the measurement of the cornea refractive power, a TV camera 7 is connected to a calculator 128 and the cornea refractive power is calculated from the signal by the instruction from a cornea measurement instruction unit 127, and the result of the calculation is indicated by an indicator 123.

A mode change instruction unit 126 is a unit for imparting a change instruction from a cornea refractive power measuring condition which is a first measurement to an eye axis length measuring condition which is a second measurement, and is connected to the motor control circuit 100. The output of an ultrasonic transmitter and receiver 121 is connected to a wave-form selection circuit 124 for discriminating the contact of the ultrasonic probe with the eye to be examined, and controls the motors 9 and 16 via the motor control circuit 100. Here, FIG. 4 shows the state in which the ultrasonic probe 12 is brought into contact with the cornea of the eye to be examined and the reflected echo signal from the eyeball then obtained, and in FIG. 4, E designates the eye to be examined, E1 denotes the cornea of the eye to be examined, E2 designates the crystalline lens, E3 denotes the retina, and S designates the reflected echo electrical signal, and the wave-form selection circuit 124 judges whether this reflected echo has been properly introduced.

For the measurement of the eye axis length, the ultrasonic probe 12 is connected to the ultrasonic transmitter and receiver 121 by a cable, and is directed therefrom to a calculator 122 for the measurement of the eye axis length, and the eye axis length is calculated thereby and the result of the calculation is indicated by the indicator 123.

The cornea refractive power data calculated by the calculator 128 and the eye axis length data calculated by the calculator 122 are supplied to an operation unit 130, in which a calculation for calculating the refractive power of an artificial crystalline lens is effected. The result of this calculation is indicated by the indicator 123.

After the measurement is completed, the motor control circuit 100 controls the motors 16 and 9 so as to rotate in the reverse direction, thereby bringing about a first condition.

In the present embodiment, the indicator 123 for indicating the results of the calculations serves also as the television monitor 8, and of course, it is also possible that the indicator 123 effects the indication and prints out the result of the measurement by a printer (not shown). Also, the calculators 122 and 128 and the operation unit 130 may be provided by a single unit. Further, the shift from the cornea refractive power measurement which is a first measuring means to the eye axis length measurement which is a second measuring means is effected by the instruction to an mode change instruction unit 126, but it is also possible to transmit a signal to the motor control circuit 100 upon completion of the output from the calculator 128 and automatically effect the change instruction.

Figure 6:
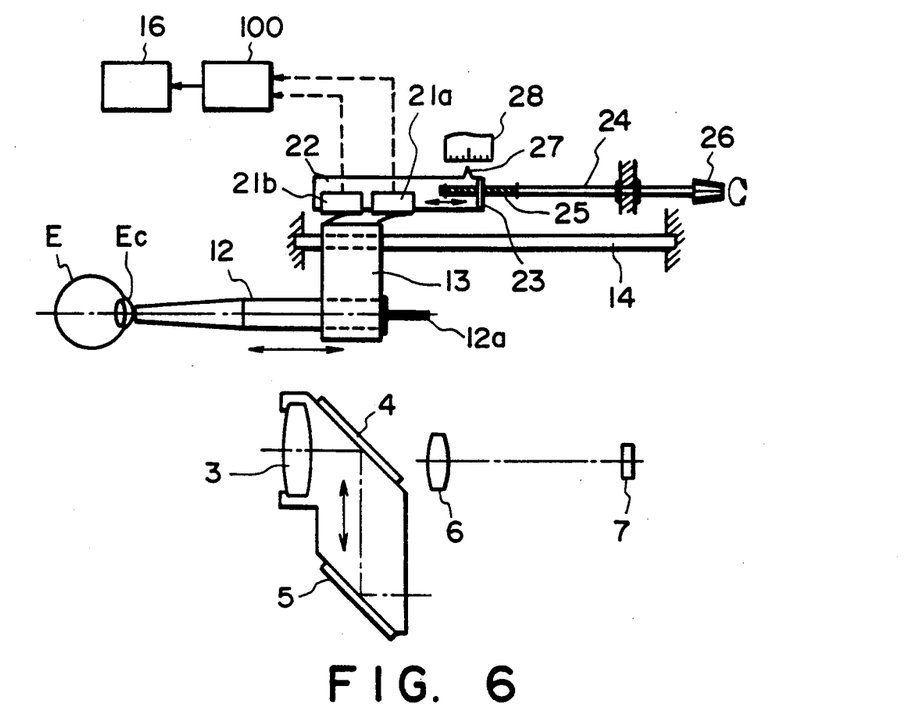

FIGS. 6 through 11 show different embodiments of the present invention. As shown in FIG. 6, switches 21a and 21b for detecting the position of the probe holder 13 are mounted on a switch bed plate 22, and the bent portion 23 of the switch bed plate 22 is threadably engaged with the male screw 25 of a feed shaft 24, and by rotating an adjust knob 26 provided at the end of the feed shaft 24, the position of the switch bed plate 22, i.e., the switches 21a and 21b, may be moved in the direction of sliding movement of the probe 12 to thereby set the switches at any position. A needle 27 is provided on the switch bed plate 22 and the set position may be read from a scale plate 28 combined with this needle 27.

When the probe 12 slides toward the eye E to be examined, the motor driving control circuit 100 drivingly controls the electric motor 16 at a high speed at the initial stage of the sliding movement, and when the probe holder 13 closes the switch 21a, the motor control circuit 100 effects the drive control of the electric motor 16 at a low speed. Further, when the probe holder 13 comes to a position for closing the switch 21b, the electric motor 16 is stopped. Thus, the change-over time can be shortened and the danger of the probe 12 striking against the cornea Ec of the eye E to be examined with a strong inertia force can be avoided.

Here, whether the position of the fore end of the ultrasonic probe 12 during the measurement of the eye axis length should be substantially brought into coincidence with the position of the cornea of the eye E to be examined during the measurement of the cornea refractive power or should be somewhat protruded in the direction of the optic axis can be set arbitrarily by the adjust knob 26.

Figure 7:
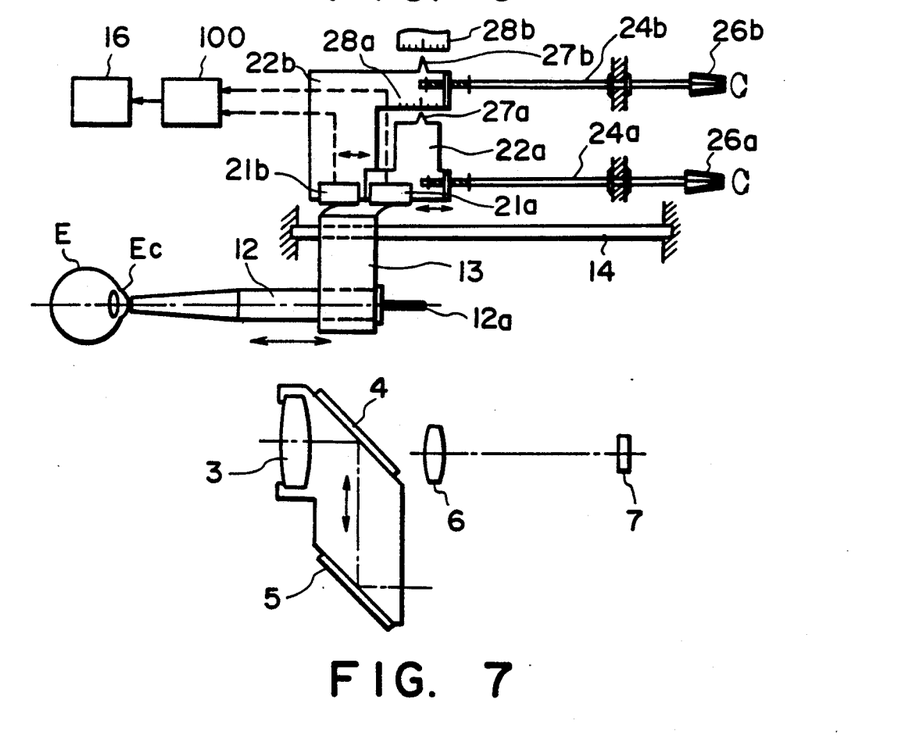

FIG. 7 shows a third embodiment of the present invention. In FIG. 7, reference characters similar to those in FIG. 6 designate similar or equivalent members. In this embodiment, switches 21a and 21b are mounted on discrete switch bed plates 22a and 22b, and the switches 21a and 21 b can be individually adjusted by respective feed shafts 24a and 24b and adjust knobs 26a and 26b. Also, a needle 27b provided on the switch bed plate 22b is combined with a scale plate 28b, and a scale plate 28a combined with a needle 27a provided on the switch bed plate 22a is provided on the switch bed plate 22b. With such a construction, the position of the switch 21a for changing the sliding speed of the prove 12 to a low speed and the position of the switch 21b for detecting the stopped position of the probe 12 can be set independently of each other and therefore, it becomes possible to freely set the time required to change over the mode from the cornea refractive power measuring mode to the eye axis length measuring mode.

Figure 8:
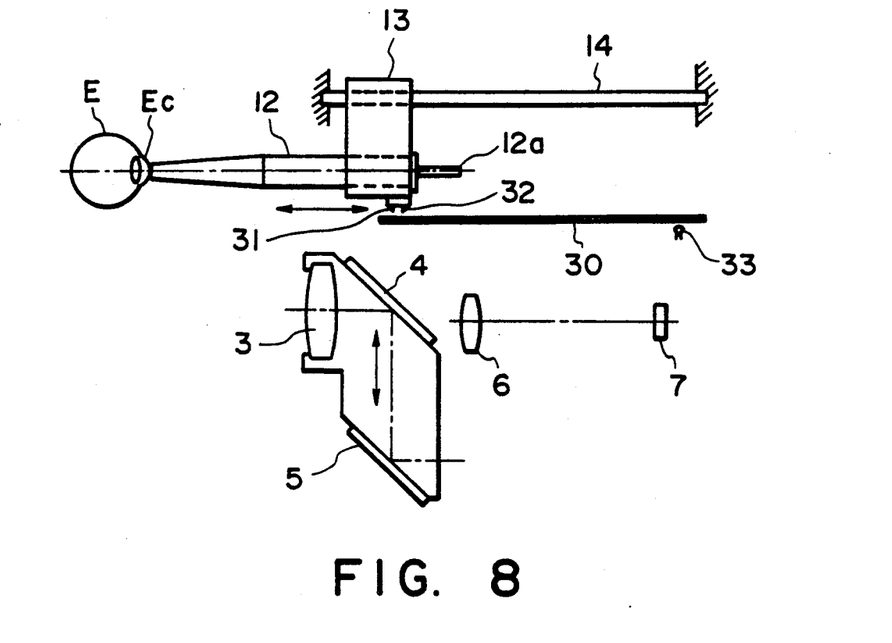
Figure 9:
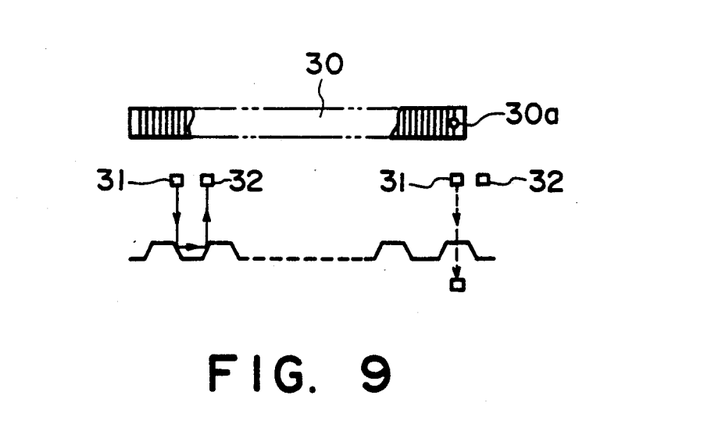
FIG. 9 is a plan view of a mark plate in the FIG. 8 embodiment.

FIG. 8 shows a fourth embodiment of the present invention. In this embodiment, as the means for detecting the position of the probe holder 13, use is made of a non-contact type photodetector comprising a mark plate 30 having a plurality of stripe-like reflecting portions and provided with a light beam transmitting hole 30a at a fiducial position, a pair of light-emitting element 31, and light-receiving element 32 provided on the probe holder 13 side, and a fiducial position detecting light-receiving element 33 disposed at the fiducial position. The light travelling from the light-emitting element 31 toward the mark plate 30 is reflected by the reflecting portions of the mark plate 30, and the reflected light is received by the light-receiving element 32. When the light-emitting element 31 is near the fiducial position, the light travelling from the light-emitting element 31 toward the mark plate 30 is received by the light-receiving element 33 through the light beam transmitting hole 30a in the mark plate 30.

Figure 10:
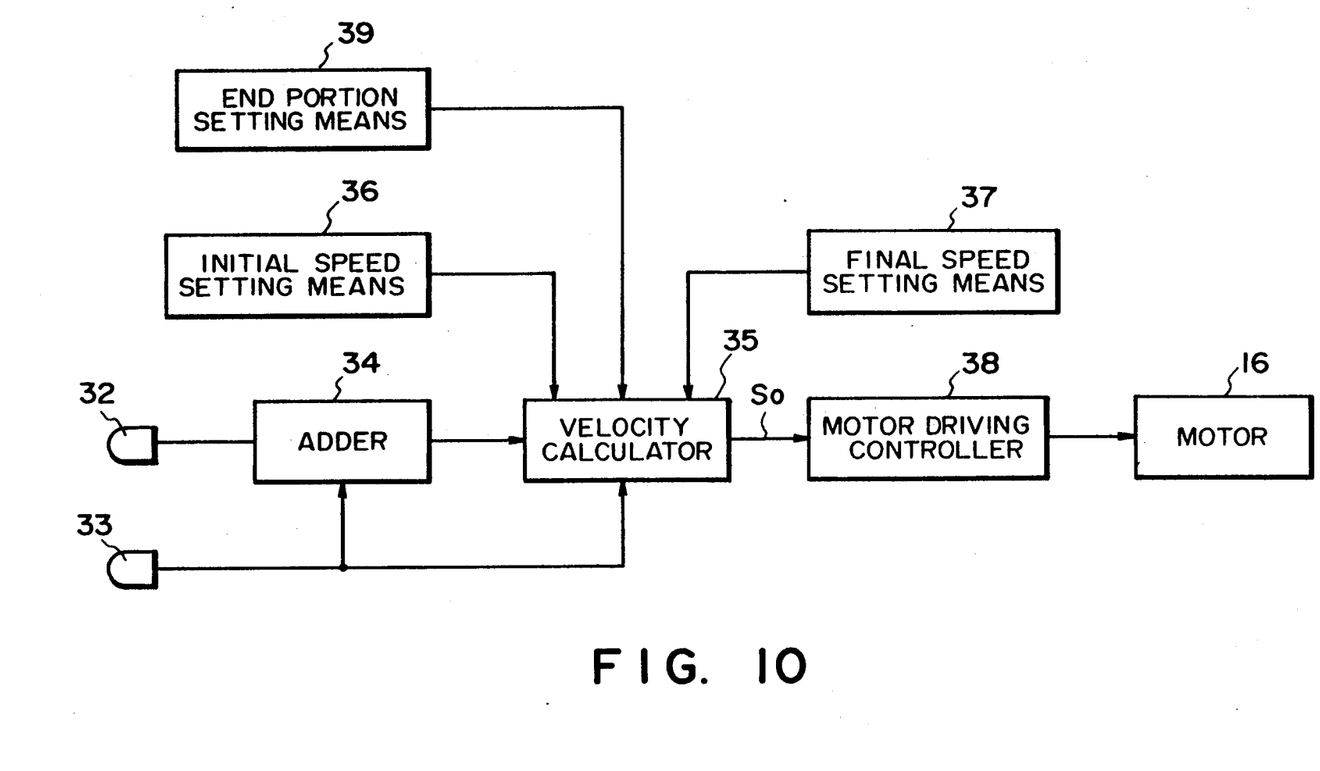
FIG. 10 is a block diagram of a signal processing system in the FIG. 8 embodiment.

FIG. 10 exemplarily shows the signal processing system in the embodiment of FIG. 8. A pulse-like signal output from the light-receiving element 32 with the sliding movement of the probe holder 13 is integrated by an adder 34 from the forward course of the probe holder 13 to the cornea to the backward course thereof from the cornea, and the addition output of the adder 34 is reset by the output signal of the light-receiving element 33. A velocity calculator 35 receives as an input the data from an initial speed setting means 36, a final speed setting means 37 and the adder 34 and calculates and outputs a velocity control signal $S_0$, and drivingly controls the electric motor 16 shown in FIG. 1 through a motor driving controller 38. The substance of the calculation by the velocity calculator 35 is to calculate the velocity change from the initial speed value by the initial speed setting means 36 to the final speed value by the final speed setting means 37 as a function relative to the output data of the adder 34, and it is possible to set any function type in the velocity calculator 35. On the other hand, the velocity calculator 35 is adapted to impart a stop instruction signal to the velocity control signal $S_0$ when the output data of the adder 34 coincides with the value of an end portion setting means 39 and when the output signal of the light-receiving element 33 is input. Again in this embodiment, the velocity control for setting the time required to change over the mode from the cornea refractive power measuring mode to the eye axis length measuring mode to the shortest time is possible. In this embodiment, the mark plate 30 has been shown as being comprises of a 1-bit encoder, but the mark plate 30 can also be comprised of a multi-bit encoder capable of reading the absolute value of the position.

In the above-described embodiments, there has been shown a case where the cornea refractive power measuring means is applied as the first measuring system for detecting the information of the eye to be examined with a predetermined distance held relative to the cornea of the eye to be examined and the ultrasonic eye axis length measuring means is applied as the second measuring system for detecting the information of the eye to be examined with the end of the detecting terminal brought into contact with the cornea and the detecting terminal is an ultrasonic probe, but this merely shows an example, and of course, other measuring means may be applied as the first measuring system and the second measuring system.

Figure 11:
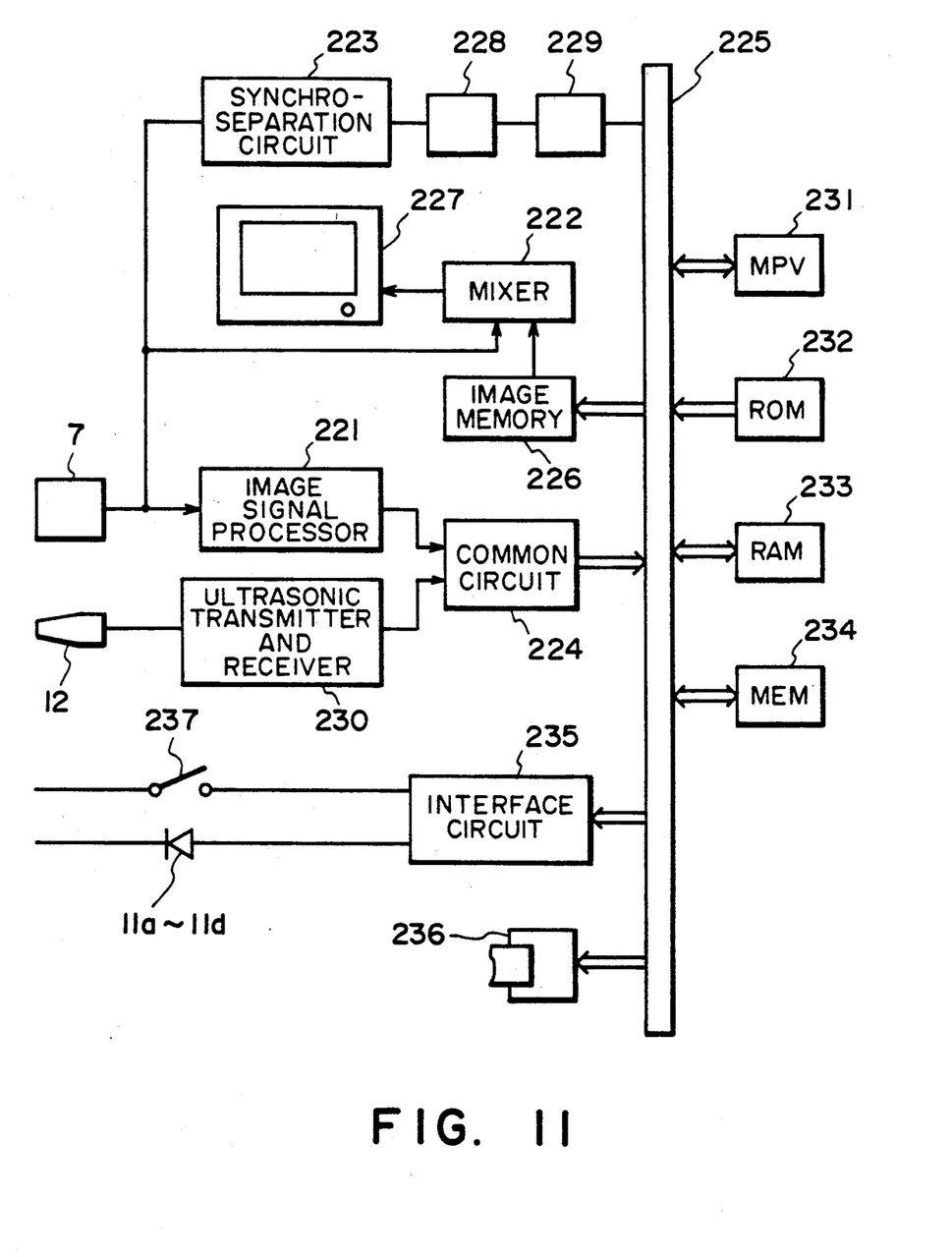
FIG. 11 shows a case where the cornea refractive power and the eye axis length are calculated by a common circuit and the refractive power of a fit in-the-eye lens is indicated.

A case where the cornea refractive power and the eye axis length are calculated by a common circuit and the refractive power of a fit in-the-eye lens is displayed will hereinafter be described with respect to FIG. 11. In FIG. 11 the output of the two-dimensional image pickup element 7 is connected to an image signal processing circuit 221, a mixer circuit 222 and a synchronous separating circuit 223, and the output of the image signal processing circuit 221 is connected to an internal bus 225 through a common circuit 224. An image memory 226 is also connected to the internal bus 225, and the output of this image memory 226 is connected to a television monitor 227 through the mixer circuit 222. The output of the synchronous separating circuit 223 is connected to the internal bus 225 through a recording circuit 228 and a memory circuit 229. The output of the ultrasonic probe 12 is connected to the internal bus 225 through an ultrasonic transmitter and receiver circuit 230 and the common circuit 224. Also connected to the internal bus 225 are a microprocessor unit (MPU) 231, a read-only memory (ROM) 232, a random access memory (RAM) 233, and a non-violate memory 234, and the output of the internal bus 225 is connected to an interface 235 and a printer 236. Further, a measuring switch 237 and light source 11a–11d are connected to the interface 235.

With regard to the cornea shape measurement, the maximum radius of curvative, the minimum radius of curvature, the mean radius of curvature, the degree of astigmatism of the cornea and the angle of astigmatism axis which are the information of the cornea shape and the degree of spherical refraction, the degree of eye refraction astigmatism and the angle of astigmatism axis which are the information of the eye refractive power are calculated from a predetermined calculation formula written in the read-only memory 232, and the result of this calculation is indicated on the television monitor 227 through the image memory 226 and the mixer circuit 222.

Also, with regard to the eye axis length measurement, the amplified echo signal is converted into a digital signal by an A/D converter in the common circuit 224, and is written into the image 226 via the internal bus 225, and an ultrasonic reflected wave signal is indicated on the television monitor 227 corresponding each part of the eye E to be examined. The microprocessor unit 231 calculates the eye axis length, the depth of the fore cell, the thickness of the crystalline lens and the thickness of the glass body from a predetermined calculation formula written in the read-only memory 232, and the result of this calculation is indicted on the television monitor 227 through the image memory 226 and the mixer circuit 222.

From the information of the cornea shape of the eye E to be examined and the measured value of the length of the predetermined region obtained in the manner described previously, the microprocessor unit 231 calculates the refractive power of the in-the-eye lens by a predetermined calculation formula written in the read-only memory 232, and the result of this calculation in indicated on the television monitor 227 through the mixer circuit 222.

We claim:

1. An ophthalmologic apparatus, comprising:
   (a) a first measuring system for detecting first information of an eye to be examined at a predetermined working distance relative to the cornea of the eye to be examined;
   (b) a second measuring system for detecting second information of the eye to be examined with a detection terminal brought into contact with the cornea of the eye to be examined;
   (c) observation means for observing a positioning alignment state of said detection terminal to the eye to be examined from a moving direction of said detection terminal, said observation means being fixed at least in the moving direction of said detection terminal during the detecting performed using said detection terminal;
   (d) driving means for moving said detection terminal relative to said first measuring system from a position at which said detection terminal is spaced apart from the cornea of the eye to be examined to a position at which said detection terminal contacts the cornea of the eye to be examined without shifting the entire apparatus in the moving direction of said detection terminal; and (e) driving control means for controlling said driving means so as to slow down at least the speed of movement of said detection terminal when said detection terminal comes near the cornea of the eye to be examined.

2. An ophthalmologic apparatus according to claim 1, wherein said driving control means is provided with detecting means for detecting that said detecting terminal comes near the cornea of the eye to be examined, and slows down the speed of movement by said detection.

3. An ophthalmologic apparatus, comprising:
(a) a first measuring system for detecting first information of an eye to be examined at a predetermined working distance relative to the cornea of the eye to be examined;
(b) a second measuring system for detecting second information of the eye to be examined with a detection terminal brought into contact with the cornea of the eye to be examined;
(c) observation means for observing a positioning alignment state of said detection terminal to the eye to be examined from a moving direction of said detection terminal, said observation means being fixed at least in the moving direction of said detection terminal during the detecting performed using said detection terminal;
(d) driving means for moving said detection terminal relative to said first measuring system from a position at which said detection terminal is spaced apart from the cornea of the eye to be examined to a position at which said detection terminal contacts the cornea of the eye to be examined without shifting the entire apparatus in the moving direction of said detection terminal; and
(e) driving control means for controlling said driving means so as to slow down at least the speed of movement of said detection terminal when said detection terminal comes near the cornea of the eye to be examined, wherein said driving means is provided with detecting means for detecting that said detection terminal comes near the cornea of the eye to be examined, and said driving means slows down the speed of movement of said detection terminal in response to detecting that said detection terminal comes near the cornea of the eye to be examines, wherein said driving control means is provided with second detecting means for detecting that said detection terminal comes near the cornea of the eye to be examined, and for producing a signal used as a stop signal to stop said driving means from driving said detection terminal.

4. An ophthalmologic apparatus, comprising:
(a) a first measuring system for detecting first information of an eye to be examined at a predetermined working distance relative to the cornea of the eye to be examined;
(b) a second measuring system for detecting second information of the eye to be examined with a detection terminal brought into contact with the cornea of the eye to be examined;
(c) observation means for observing a positioning alignment state of said detection terminal to the eye to be examined from a moving direction of said detection terminal, said observation means being fixed at least in the moving direction of said detection terminal during the detecting performed using said detection terminal;
(d) driving means for moving said detection terminal relative to said first measuring system from a position at which said detection terminal is spaced apart from the cornea of the eye to be examined to a position at which said detection terminal contacts the cornea of the eye to be examined without shifting the entire apparatus in the moving direction of said detection terminal; and
(e) driving control means for controlling said driving means so as to slow down at least the speed of movement of said detection terminal when said detection terminal comes near the cornea of the eye to be examined, wherein said driving means is provided with detecting means for detecting that said detection terminal comes near the cornea of the eye to be examined, and said driving means slows down the speed of movement of said detection terminal in response to detecting that said detection terminal comes near the cornea of the eye to be examined, wherein the position said detecting means is variable in the direction of an optical axis of said apparatus.

5. An ophthalmologic apparatus according to claim 4, further provided with means for recognizing the position of said detecting means in the direction of the optic axis.

6. An ophthalmologic apparatus according to claim 3, wherein said detecting means and said second detecting means have their positions variable in the direction of the optic axis.

7. An ophthalmologic apparatus according to claim 6, further provided with means for recognizing the positions of said detecting means and said second detecting means in the direction of the optic axis.

8. An ophthalmologic apparatus according to claim 2, wherein said second measuring system is an ultrasonic type eye axis length meter, said detecting terminal is an ultrasonic probe, and said driving control means utilizes an ultrasonic echo signal produced when the force end of said probe comes into contact with the cornea of the eye to be examined as a stop signal for said driving means.

9. An ophthalmologic apparatus according to claim 1, further having driving means for moving said detecting terminal to its retracted position after the detection of said second information of the eye to be examined is terminated.

10. An ophthalmologic apparatus according to claim 1, wherein said detecting terminal is connected to a spring biased so as to reduce the increase in the force of contact with the cornea of the eye to be examined.

11. An ophthalmologic apparatus according to claim 1, wherein said first and second measuring systems are measuring systems for detecting the cornea refractive power and the length in the direction of the eye axis, respectively, and are provided with memory means for memorizing the detected cornea refractive power and the detected length in the direction of the eye axis, calculating means for calculating the refractive power of an in-the-eye lens from the cornea refractive power and the length in the direction of the eye axis memorized by said memory means, and indicator means for indicating the output of said calculating means.

12. An ophthalmologic apparatus according to claim 1, wherein said first information of the eye to be examined and said second information of the eye to be examined are detected through a common operation circuit.

13. An ophthalmologic apparatus, comprising:

(a) an optical measuring system for detecting information of an eye to be examined, at a predetermined working distance relative to the cornea of the eye to be examined, and for detecting positional alignment of a probe relative to the eye through an optical axis of said optical measuring system;

(b) an ultrasonic measuring system for detecting dimensional information of the eye with said probe brought into contact with the cornea, said probe being movable on the optical axis of said optical measuring system;

(c) first driving means for positioning an objective lens unit of said optical measuring system on the optical axis;

(d) second driving means for moving said probe on the optical axis; and p1 (e) mode change instruction means which, at the performance of the ultrasonic measurement, instructs said first driving means to retract said objective lens unit from the optical axis and instructs said second driving means to move said probe into contact with the cornea, wherein said second driving means reduces the speed of said probe near the cornea.

14. An ophthalmologic apparatus, comprising:

(a) an optical system for detecting positional alignment of a probe relative to an eye to be examined through an optical axis of said optical system;

(b) a measuring system for detecting information of the eye with said probe brought into contact with the cornea, said probe being movable on the optical axis of said optical system;

(c) a first driving means for positioning an objective lens unit of said optical system on the optical axis;

(d) a second driving means for moving said probe on said optical axis; and (e) mode change instruction means which at the performance of the measurement by said measuring system instructs causes said first driving means to retract said objective lens unit from the optical axis, and instructs said second driving means to move said probe brought into contact with the cornea, wherein said second driving means reduces the speed of said probe near the cornea.

15. An ophthalmologic apparatus, comprising:

(a) an optical system for detecting positional alignment of a probe relative to an eye to be examined through an optical axis of said optical system;

(b) a measuring system for detecting information of the eye with the probe brought into contact with the cornea of the eye, the probe being movable on the optical axis of said optical system;

(c) first driving means for positioning said optical system on the optical axis;

(d) second driving means for moving the probe on the optical axis; and (e) mode change instruction means, for instructing said first driving means to retract at least one optical element of said optical system from the optical axis, and for instructing said second driving means to reduce the speed of the probe near the cornea so that said measuring system can perform its detecting operation.

* * * * *

UNITED STATES PATENT AND TRADEMARK OFFICE
CERTIFICATE OF CORRECTION

PATENT NO. : 5,116,114
DATED : May 26, 1992
INVENTOR(S) : Nakamura et al.

It is certified that error appears in the above-identified patent and that said Letters Patent is hereby corrected as shown below:

COLUMN 2:

Line 54, "numerals 8" should read --numerals 18--.

Line 62, "tween the" should read --tween, the--.

COLUMN 3:

Line 64, "with" should be deleted.

COLUMN 4:

Line 43, "with" should be deleted.

Line 46, "probe" should read --probe 12--.

Line 67, "revolve" should read --rotate--.

COLUMN 5:

Line 61, "the" should read --an--; and after "to", "an" should read --the--.

UNITED STATES PATENT AND TRADEMARK OFFICE
CERTIFICATE OF CORRECTION

PATENT NO. : 5,116,114           Page 2 of 3

DATED : May 26, 1992

INVENTOR(S) : Nakamura et al.

It is certified that error appears in the above-identified patent and that said Letters Patent is hereby corrected as shown below:

COLUMN 6:

Line 36, "21 b" should read --21b--.

Line 43, "prove" should read --probe--.

COLUMN 7:

Line 31, "comprises" should read --comprised--.

Line 53, "FIG. 11" should read "FIG. 11,--.

COLUMN 8:

Line 5, "light source 11a-11d" should read --light sources 11a-11d--

Line 23, "image 226" should read --image memory 226--.

Line 31, "indicted" should read --indicated--.

Line 40, "in" should read --is--.

COLUMN 9:

Line 46, "examines," should read --examined,--

UNITED STATES PATENT AND TRADEMARK OFFICE
CERTIFICATE OF CORRECTION

PATENT NO.  :  5,116,114

DATED       :  May 26, 1992

INVENTOR(S) :  Nakamura et al.

It is certified that error appears in the above-identified patent and that said Letters Patent is hereby corrected as shown below:

COLUMN 10:

Line 20, "position" should read --position of--.

Line 39, "force" should read --fore--.

COLUMN 11:

Line 16, "pl(e)" should read -- ¶ (e)--.

COLUMN 12:

Line 7, "causes" should be deleted.

Signed and Sealed this

Thirty-first Day of August, 1993

Attest:

BRUCE LEHMAN

*Attesting Officer*       *Commissioner of Patents and Trademarks*